(12) United States Patent
Wang et al.

(10) Patent No.: US 10,344,122 B2
(45) Date of Patent: Jul. 9, 2019

(54) PREPARING METHOD OF ALIPHATIC POLYCARBONATE

(71) Applicant: CHENGDU ORGANIC CHEMICALS CO., LTD. CHINESE ACADEMY OF SCIENCES, Chengdu (CN)

(72) Inventors: Gongying Wang, Chengdu (CN); Ziqing Wang, Chengdu (CN); Xiangui Yang, Chengdu (CN); Hua Zhang, Chengdu (CN); Jianguo Li, Chengdu (CN); Shaoying Liu, Chengdu (CN); Jie Yao, Chengdu (CN)

(73) Assignee: CHENGDU ORGANIC CHEMICALS CO., LTD., CAS, Chengdu (CN)

( * ) Notice: Subject to any disclaimer, the term of this patent is extended or adjusted under 35 U.S.C. 154(b) by 18 days.

(21) Appl. No.: 15/721,739

(22) Filed: Sep. 30, 2017

(65) Prior Publication Data
US 2018/0086880 A1    Mar. 29, 2018

Related U.S. Application Data

(63) Continuation of application No. PCT/CN2015/076131, filed on Apr. 9, 2015.

(51) Int. Cl.
| | |
|---|---|
| *C08G 64/02* | (2006.01) |
| *C08G 64/30* | (2006.01) |
| *C07C 68/06* | (2006.01) |
| *C07C 69/96* | (2006.01) |
| *C08G 64/16* | (2006.01) |

(52) U.S. Cl.
CPC .............. *C08G 64/02* (2013.01); *C07C 68/06* (2013.01); *C07C 69/96* (2013.01); *C08G 64/16* (2013.01); *C08G 64/30* (2013.01); *C08G 64/305* (2013.01)

(58) Field of Classification Search
USPC .................................................. 528/196, 198
See application file for complete search history.

(56) References Cited

U.S. PATENT DOCUMENTS

2003/0204042 A1* 10/2003 Moethrath ........... C08G 64/305
                                                              528/196

FOREIGN PATENT DOCUMENTS

| CN | 1561356 A    | 1/2005  |
|----|--------------|---------|
| CN | 101701062 A  | 5/2010  |
| JP | 2001270938 A | 10/2001 |
| WO | 2009063768 A1| 5/2009  |

* cited by examiner

*Primary Examiner* — Terressa Boykin
(74) *Attorney, Agent, or Firm* — Hemisphere Law, PLLC; Zhigang Ma

(57) ABSTRACT

A preparing method of an aliphatic polycarbonate is provided to synthesize oligomer monomers by a transesterification reaction of carbonic acid dialkyl esters and aliphatic diols with accelerants in an atmosphere of a protective gas, and generate an aliphatic polycarbonate polymer by a polycondensation reaction of the oligomer monomers in a condition of high temperature and low pressure. According to the disclosure, environmentally friendly compounds with low boiling points and low costs are utilized as the accelerants to substitute the enzyme or acid-base catalysts to prepare aliphatic polycarbonate polymers in the prior art, and the cost is reduced; meanwhile, in the process of generating the aliphatic polycarbonate polymers, the accelerants can be removed from the reaction system along with the pressure reduced in the reaction system. The synthesis system is simple; moreover, the aliphatic polycarbonate obtained by the preparing method provided by the disclosure has merits such as superior colors.

3 Claims, 1 Drawing Sheet

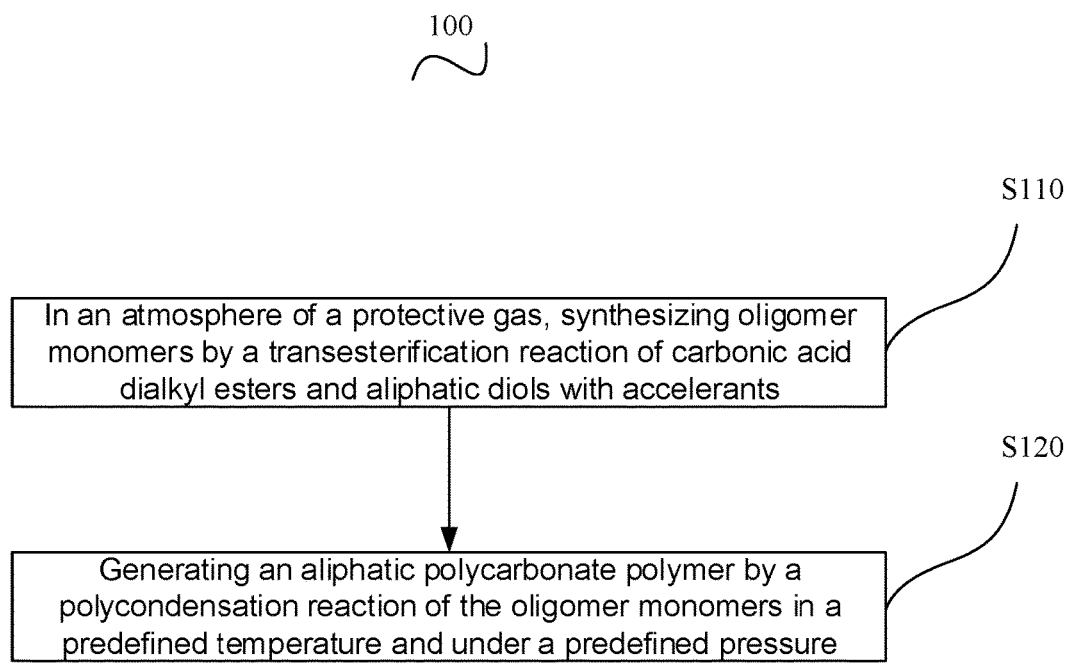

PREPARING METHOD OF ALIPHATIC POLYCARBONATE

FIELD OF THE DISCLOSURE

The disclosure relates to a polymer synthesis technical field, and more particularly to a preparing method of an aliphatic polycarbonate.

BACKGROUND

Aliphatic polycarbonates are a sort of polymers with good mechanical properties, which are widely applied in realms such as food packaging, plastic thin films, etc. Meanwhile, aliphatic polycarbonates likewise have superior biocompatibility and biodegradation. Particularly functional materials can be obtained by improving aliphatic polycarbonates, which have been comprehensively used in aspects such as medicine carriers, tissue engineering materials, medical sutures, medical screws and the like. As a result, the aliphatic polycarbonates always are the focus attracting attention of chemists.

Accounts of Chemical Research 37(2004) 836 and Angew Chem Int Ed 43(2004)3574 reported that Mn of aliphatic polycarbonates prepared by copolymerizing $CO_2$/epoxides with [Cr(salen)] and [Co(salen)] as catalysts respectively can be up to $8.9 \times 10^3$ and $3.04 \times 10^4$. As the catalysts can hardly be segregated thoroughly, a great deal of $Co^{2+}$ and $Cr^{2+}$ remain in the polymers. The types of metallic ions are severely noxious, and the application of the polymers will bring huge safety risks; moreover, zinc glutaric acid is regarded as a kind of catalysts with the most enormous potential in industry. Macromolecules 35(2002)6494 discovered that catalytic efficiencies of the kind of catalysts mostly are relatively low, and each gram of the catalysts merely can generate tens of or less than ten grams of products. Therefore, consumption of the catalysts has to be increased to achieve mass production of products, which raises costs of the products significantly and affects performance of the products; Chinese patents CN 101440159A and CN 1583825A published the method of preparing aliphatic polycarbonates with transition metal cyanides as the catalyst, but the heavy metal ions in the sort of catalyst can hardly be segregated, and the residual catalyst will degrade the quality of the polymers. Molecular weights of the polymers also are relatively low, which are not fit for used as plastic directly; a patent CN 102197063A disclosed a method of removing metal complexes as catalysts from aliphatic polycarbonates, but processes of the method are too complex to reduce the costs of polymers.

Adopting melt transesterification to synthesize polymers has advantages such as simply processes, high catalytic efficiencies and environmentally safety. Therefore, the melt transesterification recently receives broad attention from APCs researchers. American Cross research group (Macromolecular 2007, 40:7934) utilized the diethyl carbonate and 1,4-butylene glycol to synthesize APCs by melt transesterification with a lipase as the catalyst, but the maximal weight-average molecular weight Mw of the prepared polymer is less than $6.0 \times 10^4$. A patent CN 101643542A and the paper Polym. Int., 60(2011)1060 employed $TiO_2/SiO_2$(PVP) as the catalyst to prepare APCs by a novel method of melt transesterification, and the number-average molecular weight of the prepared polymer tested by GPC can be up to $1.8 \times 10^5$, which can meet the requirement of the number-average molecular weight of plastic grade APCs, and the value is $7.0 \times 10^4$. U.S. Pat. No. 8,168,728 B2 used titanium tetrabutoxide as the catalyst in the melt transesterification reaction of methyl carbonates and diols to prepare the polycarbonate. The content of terminal hydroxyl in the polymer prepared by the method is high and the molecular weight is low, which cannot be applied in plastic industries directly. A patent JPH08143656 reported a preparation method of aliphatic polycarbonate with high molecular weight. The method used zinc acetate dihydrate and zirconium acetylacetonate as the catalysts to synthesize block APCs polymers whose number-average molecular weight Mn is larger than 15000 by the transesterification reaction of diphenyl carbonates, aliphatic dicarboxylic ester and diols. Recently, U.S. Pat. No. 9,447,234 B2 reported to catalyze dimethyl carbonates and diols with sodium methoxide by the melt transesterification reaction to synthesize the APCs new catalysis system. The weight-average molecular weight Mw of obtained polymers can be up to $2.48 \times 10^5$.

It can be learnt from the methods above that molecular weights of polymers obtained by the melt transesterification catalyzed by bio-enzyme generally are relatively low, which cannot be applied as plastic directly; but in other acid-base catalysis systems, catalysts and products can hardly be separated thoroughly. The remaining catalysts will affect colors and thermostability of the product, as well as generating toxicity out of the product. Nowadays, a method of dissolving polymers in chloroform and filtering to segregate catalysts is commonly used in basic research papers. The adoption of the method obviously will generate a great amount of poisonous waste, which cannot satisfy the environmental request for mass production, and the method cannot thoroughly separate the catalysts from the product.

SUMMARY

Aiming at shortcomings such as high costs, difficulties in segregating catalysts from products, relatively poor comprehensive properties of final products and the like, it is necessary to provide a preparing method of an aliphatic polycarbonate.

In order to achieve the objective above, the disclosure employs following embodiments.

A preparing method of an aliphatic polycarbonate includes following steps: in an atmosphere of a protective gas, synthesizing oligomer monomers by a transesterification reaction of carbonic acid dialkyl esters and aliphatic diols with accelerants; generating an aliphatic polycarbonate polymer by a polycondensation reaction of the oligomer monomers in high temperatures and under low pressures.

In some embodiments, the protective gas is nitrogen.

In some embodiments, the carbonic acid dialkyl esters are one or a combination of some of dimethyl carbonates, diethyl carbonates and diphenyl carbonates.

In some embodiments, the aliphatic diols are one or more of ethylene glycols, 1,2-propylene glycols, 1,3-propylene glycols, 1,3-butyleneglycols, 1,4-butyleneglycols, 1,5-pentanediols, neopentyl glycols, 1,6-hexanediols, 1,3-hexandiols and 1,12-dodecanediols, one or a combination of some of 1,4-cyclohexanedimethanols, 1,4-cyclohexane diols, isosorbides and 2,2,4,4-tetramethyl-1,3-tetramethylene glycols.

In some embodiments, the accelerants are one or a combination of some of phenols, water, methanol, ethanol, o-cresols, m-cresols, p-cresols, 2,4-xylenols, 2,5-xylenols and 3,5-xylenols.

In some embodiments, a pH value of the accelerants is 2.0-10.0.

In some embodiments, a mole ratio of the aliphatic diols to the carbonic acid dialkyl esters is 1:0.95~4.0; a mole ratio of the accelerants to the carbonic acid dialkyl esters is 0.1~10:1.

In some embodiments, a heating process of the transesterification reaction is: first reacting at 40-110° C. for 0.5-5 h, then reflux reacting with a heating rate of 1° C./min at 160-300° C. for 1-5 h.

In some embodiments, the oligomer monomer is

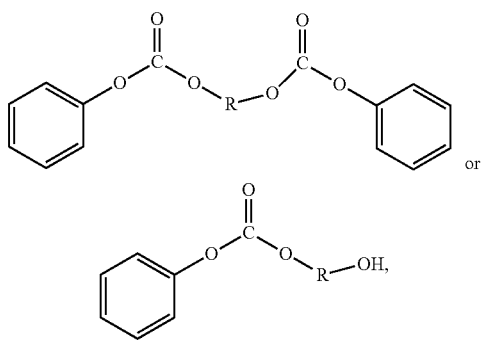

where R is an alkyl.

In some embodiments, the high temperatures are reaction temperatures at 150-300° C., the low pressures are pressures lower than 300 pa, and a reaction period is 0.5-24 h.

In some embodiments, a weight-average molecular weight $M_w$ of the aliphatic polycarbonate polymer is above $1.22 \times 10^5$.

By adopting the aforementioned embodiments, beneficial effects of the disclosure are as follows.

According to the preparing method of the aliphatic polycarbonate provided by the disclosure, in the atmosphere of the protective gas, oligomer monomers are synthesized by a transesterification reaction of carbonic acid dialkyl esters and aliphatic diols with accelerants. The aliphatic polycarbonate polymer is generated by a polycondensation reaction of the oligomer monomers in high temperatures and under low pressures. According to the disclosure, environmentally friendly compounds with low boiling points and low costs are utilized as the accelerants to substitute the enzyme or acid-base catalysts to prepare aliphatic polycarbonate polymers in the prior art, and the cost is reduced; meanwhile, in the process of generating the aliphatic polycarbonate polymers, the accelerants can be removed from the reaction system along with the pressure reduced in the reaction system. The synthesis system is simple; moreover, the aliphatic polycarbonate obtained by the preparing method provided by the disclosure has merits such as superior colors, high purity and good thermostability. The prepared weight-average molecular weight $M_w$ of the aliphatic polycarbonate polymer is above $1.22 \times 10^5$. Meanwhile, the molecular weight can be controlled by altering the sort and amount of the accelerants, which can be applied in fields such as bio-medicine, environmental engineering and plastic products.

BRIEF DESCRIPTION OF THE DRAWINGS

FIG. 1 is a flowchart of steps of a preparing method of an aliphatic polycarbonate provided by the disclosure.

DETAILED DESCRIPTION OF PREFERRED EMBODIMENTS

In order to better clarify the objective, embodiments and technical effects of the disclosure, concrete embodiments of the disclosure will be illustrated with reference to accompanying drawings as follows. The described concrete embodiments are for explaining the disclosure instead of limiting the disclosure.

In the disclosure, relational terms such as "first" and "second" are merely for the purpose of distinguishing one object or process from another object or process, which do not request or imply any practical relation or sequence between the objects or processes. Moreover, terms "include", "contain" or the like tends to indicate non-exclusive inclusion to make processes, methods, objects or devices with a series of factors to include the factors and other factors that are not clearly listed, or including inherent factors of the processes, methods, objects or devices. Without further limitation, a factor restricted by a sentence "include a" does not exclude other identical factors included in the processes, methods, objects or devices with the factors.

Referring to FIG. 1, FIG. 1 is a flowchart 100 of steps of a preparing method of an aliphatic polycarbonate provided by the disclosure, including following steps.

Step S110: in an atmosphere of a protective gas, synthesizing oligomer monomers by a transesterification reaction of carbonic acid dialkyl esters and aliphatic diols with accelerants.

Preferably, the protective gas is nitrogen.

Preferably, the carbonic acid dialkyl esters are one or a combination of some of dimethyl carbonates, diethyl carbonates and diphenyl carbonates.

Preferably, the aliphatic diols are one or more of ethylene glycols, 1,2-propylene glycols, 1,3-propylene glycols, 1,3-butyleneglycols, 1,4-butyleneglycols, 1,5-pentanediols, neopentyl glycols, 1,6-hexandiols, 1,3-hexandiols and 1,12-dodecanediols, one or a combination of some of 1,4-cyclohexanedimethanols, 1,4-cyclohexane diols, isosorbides and 2,2,4,4-tetramethyl-1,3-tetramethylene glycols.

Preferably, the accelerants are one or a combination of some of phenols, water, methanol, ethanol, o-cresols, m-cresols, p-cresols, 2,4-xylenols, 2,5-xylenols and 3,5-xylenols.

Preferably, a pH value of the accelerants is 2.0-10.0.

Preferably, a mole ratio of the aliphatic diols to the carbonic acid dialkyl esters is 1:0.95~4.0; a mole ratio of the accelerants to the carbonic acid dialkyl esters is 0.1~10:1.

Preferably, a heating process of the transesterification reaction is: first reacting at 40-110° C. for 0.5-5 h, then reflux reacting with a heating rate of 1° C./min at 160-300° C. for 1-5 h.

Preferably, the oligomer monomer is

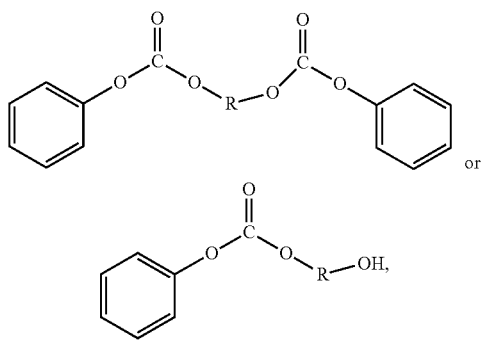

where R is an alkyl.

Step S120: generating an aliphatic polycarbonate polymer by a polycondensation reaction of the oligomer monomers in a condition of high temperature and low pressure.

Preferably, the high temperature is in a range of 150-300° C. The low pressure is lower than 300 pa, and a reaction period is 0.5-24 h.

As the accelerants are compounds with low boiling points, after the transesterification reaction, the accelerants can be removed from the reaction system in the process of reducing the pressure along with the condition of the system turned to be high temperature and low pressure.

Preferably, a weight-average molecular weight $M_w$ of the aliphatic polycarbonate polymer is above $1.22 \times 10^5$.

The disclosure will be further illustrated by the following embodiments. The embodiments are merely for an objective of illustration rather than limiting the scope of the disclosure. Except for any given note, the test methods in the embodiments are processed according to the conventional condition.

Embodiment 1

Diphenyl carbonates, 1,4-butyleneglycols and phenols are added in a reactor. A mole ratio of the three materials in the mixture is 1:1:1. The mixture is fast stirred in the $N_2$ at 90° C. for 1 h, and is heated up to 220° C. with a heating ratio of 1° C./min till no fraction is steamed out. And the pressure of the reaction system is reduced to below 300 Pa. Polymers obtained after reaction at the temperature for 2 h are aliphatic polycarbonate materials. The molecular weight of the polymers is tested by gel chromatography. The results are $M_w=5.5 \times 10^4$, $M_n=3.6 \times 10^4$, and PDI=1.53.

Embodiment 2

Dimethyl carbonates, 1,4-butyleneglycols and phenols are added in a reactor. A mole ratio of the three materials in the mixture is 2:1:1. The mixture is fast stirred in the $N_2$ at 90° C. for 1 h, and is heated up to 190° C. with a heating ratio of 1° C./min till no fraction is steamed out. And the pressure of the reaction system is reduced to below 300 Pa. Polymers obtained after reaction at the temperature for 2 h are aliphatic polycarbonate materials. The molecular weight of the polymers is tested by gel chromatography. The results are $M_w=4.3 \times 10^4$, $M_n=2.7 \times 10^4$, and PDI=1.59.

Embodiment 3

Diphenyl carbonates, 1,4-butyleneglycols and distilled water are added in a reactor. A mole ratio of the three materials in the mixture is 1:1:1. The mixture is fast stirred in the $N_2$ at 90° C. for 1 h, and is heated up to 220° C. with a heating ratio of 1° C./min till no fraction is steamed out. And the pressure of the reaction system is reduced to below 300 Pa. Polymers obtained after reaction at the temperature for 2 h are aliphatic polycarbonate materials. The molecular weight of the polymers is tested by gel chromatography. The results are $M_w=1.22 \times 10^5$, $M_n=7.7 \times 10^4$, and PDI=1.58.

Embodiment 4

Diphenyl carbonates, 1,6-hexandiols and distilled water are added in a reactor. A mole ratio of the three materials in the mixture is 1:1:1. The mixture is fast stirred in the $N_2$ at 90° C. for 1 h, and is heated up to 220° C. with a heating ratio of 1° C./min till no fraction is steamed out. And the pressure of the reaction system is reduced to below 300 Pa. Polymers obtained after reaction at the temperature for 2 h are aliphatic polycarbonate materials. The molecular weight of the polymers is tested by gel chromatography. The results are $M_w=9.9 \times 10^4$, $M_n=6.3 \times 10^4$, and PDI=1.6.

Embodiment 5

Diphenyl carbonates, 1, 4-butyleneglycols and phenols are added in a reactor. A mole ratio of the three materials in the mixture is 1:1:3. The mixture is fast stirred in the $N_2$ at 90° C. for 1 h, and is heated up to 220° C. with a heating ratio of 1° C./min till no fraction is steamed out. And the pressure of the reaction system is reduced to below 300 Pa. Polymers obtained after reaction at the temperature for 2 h are aliphatic polycarbonate materials. The molecular weight of the polymers is tested by gel chromatography. The results are $M_w=1.15 \times 10^5$, $M_n=7.3 \times 10^4$, and PDI=1.57.

Embodiment 6

Diphenyl carbonates, 1,4-butyleneglycols and distilled water are added in a reactor. A mole ratio of the three materials in the mixture is 1:1:1. The pH value of the distilled water is adjusted to be 5 by $HNO_3$. The mixture is fast stirred in $N_2$ at 90° C. for 1 h, and is heated up to 220° C. with a heating ratio of 1° C./min till no fraction is steamed out. And the pressure of the reaction system is reduced to below 300 Pa. Polymers obtained after reaction at the temperature for 2 h are aliphatic polycarbonate materials. The molecular weight of the polymers is tested by gel chromatography. The results are $M_w=1.03 \times 10^5$, $M_n=6.5 \times 10^4$, and PDI=1.58.

Embodiment 7

Diphenyl carbonates, 1,4-butyleneglycols and distilled water are added in a reactor. A mole ratio of the three materials in the mixture is 0.96:1:3. The mixture is fast stirred in $N_2$ at 90° C. for 1 h, and is heated up to 220° C. with a heating ratio of 1° C./min till no fraction is steamed out. And the pressure of the reaction system is reduced to below 300 Pa. Polymers obtained after reaction at the temperature for 2 h are aliphatic polycarbonate materials. The molecular weight of the polymers is tested by gel chromatography. The results are $M_w=9.8 \times 10^5$, $M_n=6.2 \times 10^4$, and PDI=1.6.

Embodiment 8

Diphenyl carbonates, 1,4-butyleneglycols and phenols are added in a reactor. A mole ratio of the three materials in the mixture is 1:1:1. The mixture is fast stirred in $N_2$ at 90° C. for 1 h, and is immediately heated up to 220° C. till no fraction is steamed out. And the pressure of the reaction system is reduced to below 300 Pa. Polymers obtained after reaction at the temperature for 2 h are aliphatic polycarbonate materials. The molecular weight of the polymers is tested by gel chromatography. The results are $M_w=8.5 \times 10^4$, $M_n=5.6 \times 10^4$, and PDI=1.52.

Embodiment 9

Diphenyl carbonates, 1,4-butyleneglycols and distilled water are added in a reactor. A mole ratio of the three materials in the mixture is 1:1:1. The mixture is fast stirred in $N_2$ at 90° C. for 1 h, and is heated up to 220° C. with a heating ratio of 1° C./min till no fraction is steamed out. And the pressure of the reaction system is reduced to below 300 Pa. Polymers obtained after reaction at 250° C. for 6 h are aliphatic polycarbonate materials. The molecular weight of the polymers is tested by gel chromatography. The results are $M_w=1.01\times10^5$, $M_n=6.0\times10^4$, and PDI=1.68.

Embodiment 10

Diphenyl carbonates, 1,4-butyleneglycols and diphenols are added in a reactor. A mole ratio of the three materials in the mixture is 1:1:1. The mixture is fast stirred in $N_2$ at 90° C. for 1 h, and is heated up to 220° C. with a heating ratio of 1° C./min till no fraction is steamed out. And the pressure of the reaction system is reduced to below 300 Pa. Polymers obtained after reaction at the same temperature for 2 h are aliphatic polycarbonate materials. The molecular weight of the polymers is tested by gel chromatography. The results are $M_w=2.8\times10^4$, $M_n=2.1\times10^4$, and PDI=1.37.

The foregoing embodiments merely preferred embodiments of the disclosure rather than any limitation of the disclosure. Even though the disclosure has been disclosed by preferred embodiments above, they are not for restricting the disclosure. Equivalent embodiments obtained by modifying the embodiments disclosed previously according to the contents and spirit of the disclosure achieved by a person skilled in the art are all included in the protection scope of the disclosure.

What is claimed is:

1. A preparing method of an aliphatic polycarbonate comprising following steps:
   in an atmosphere of a protective gas, synthesizing oligomer monomers by a transesterification reaction of carbonic acid dialkyl esters and aliphatic diols with accelerants;
   generating an aliphatic polycarbonate polymer by a polycondensation reaction of the oligomer monomers in a predefined temperature and under a predefined pressure;
   wherein the carbonic acid dialkyl ester is diphenyl carbonates, the aliphatic diols is 1,4-butyleneglycols, the accelerant is distilled water, and a mole ratio of diphenyl carbonates, 1, 4-butyleneglycols, and distilled water is 0.96:1:3;
   wherein a mixture of diphenyl carbonates, 1, 4-butyleneglycols, and distilled water is added in a reactor and stirred in $N_2$ at 90° C. for 1 h, and then is heated up to 220° C. with a heating ratio of 1° C./min till no fraction is steamed out, a pressure of the reaction system is reduced to below 300 Pa, after the reaction at the temperature for 2 h, a weight-average molecular weight $M_w$ of the obtained aliphatic polycarbonate polymer is $9.8\times10^5$.

2. A preparing method of an aliphatic polycarbonate comprising following steps:
   in an atmosphere of a protective gas, synthesizing oligomer monomers by a transesterification reaction of carbonic acid dialkyl esters and aliphatic diols with accelerants;
   generating an aliphatic polycarbonate polymer by a polycondensation reaction of the oligomer monomers in a predefined temperature and under a predefined pressure;
   wherein the carbonic acid dialkyl ester is diphenyl carbonates, the aliphatic diols is 1,4-butyleneglycols, the accelerant is distilled water, and a mole ratio of diphenyl carbonates, 1, 4-butyleneglycols, and distilled water is 1:1:1;
   wherein a mixture of diphenyl carbonates, 1, 4-butyleneglycols, and distilled water is added in a reactor and stirred in $N_2$ at 90° C. for 1 h, and then is heated up to 220° C. with a heating ratio of 1° C./min till no fraction is steamed out, a pressure of the reaction system is reduced to below 300 Pa, after the reaction at the temperature for 2 h, a weight-average molecular weight $M_w$ of the obtained aliphatic polycarbonate polymer is $1.22\times10^5$.

3. A preparing method of an aliphatic polycarbonate comprising following steps:
   in an atmosphere of a protective gas, synthesizing oligomer monomers by a transesterification reaction of carbonic acid dialkyl esters and aliphatic diols with accelerants;
   generating an aliphatic polycarbonate polymer by a polycondensation reaction of the oligomer monomers in a predefined temperature and under a predefined pressure;
   wherein the carbonic acid dialkyl ester is diphenyl carbonates, the aliphatic diols is 1,4-butyleneglycols, the accelerants is phenols, and a mole ratio of diphenyl carbonates, 1, 4-butyleneglycols, and phenols is 1:1:3;
   wherein a mixture of diphenyl carbonates, 1, 4-butyleneglycols, and phenols is added in a reactor and stirred in $N_2$ at 90° C. for 1 h, and then is heated up to 220° C. with a heating ratio of 1° C./min till no fraction is steamed out, a pressure of the reaction system is reduced to below 300 Pa, after the reaction at the temperature for 2 h, a weight-average molecular weight $M_w$ of the obtained aliphatic polycarbonate polymer is $1.15\times10^5$.

* * * * *